(12) United States Patent
Kang et al.

(10) Patent No.: US 11,826,468 B2
(45) Date of Patent: Nov. 28, 2023

(54) INSOLUBLE ACTIVE SUBSTANCE CARRIER COMPRISING TRANSFERSOME

(71) Applicant: Amorepacific Corporation, Seoul (KR)

(72) Inventors: Shinbeom Kang, Yongin-si (KR); Byungryol Paik, Yongin-si (KR); Chaeyeon Song, Yongin-si (KR); Soonae An, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 17/669,461

(22) Filed: Feb. 11, 2022

(65) Prior Publication Data

US 2022/0257513 A1    Aug. 18, 2022

(30) Foreign Application Priority Data

Feb. 18, 2021  (KR) ................ 10-2021-0022078

(51) Int. Cl.
| | | |
|---|---|---|
| *A61K 9/127* | (2006.01) | |
| *A61K 31/575* | (2006.01) | |
| *A61K 8/14* | (2006.01) | |

(52) U.S. Cl.
CPC .............. *A61K 9/1272* (2013.01); *A61K 8/14* (2013.01); *A61K 31/575* (2013.01)

(58) Field of Classification Search
CPC ...... A61K 9/1272; A61K 8/14; A61K 31/575; A61K 8/39; A61K 8/553; A61K 8/60; A61K 9/0014; A61K 9/1075; A61K 47/14; A61K 47/24; A61K 8/44; A61K 8/4993; A61K 8/602; A61K 8/63; A61K 8/64; A61K 8/86; A61K 8/922; A61K 31/57; A61K 45/00; A61K 47/10; A61K 47/183; A61K 47/26; A61K 47/42; A61K 47/44; A61K 2800/10; A61K 8/31; A61K 8/891; A61K 9/1271; A61K 31/56; A61K 2800/52; A61Q 19/00
See application file for complete search history.

(56) References Cited

U.S. PATENT DOCUMENTS

2008/0311184 A1\*  12/2008  Cevc ................ A61K 9/1271
                                                                424/94.1
2015/0335756 A1    11/2015  Lee et al.

FOREIGN PATENT DOCUMENTS

| CN | 105012956 A | 11/2015 |
|---|---|---|
| CN | 108324687 A | 7/2018 |

(Continued)

OTHER PUBLICATIONS

Pena-Rodriguez, E., et al Pharmaceutics, vol. 12, pp. 1-14, 1999.\*

(Continued)

*Primary Examiner* — Gollamudi S Kishore
(74) *Attorney, Agent, or Firm* — Sughrue Mion, PLLC

(57) ABSTRACT

A carrier for an insoluble active substance is disclosed. The carrier contains transfersome that includes an insoluble active substance in a high content and can stabilize the insoluble active substance. In addition, since the carrier has a small particle size, it is possible to promote the delivery of the insoluble active substance into a body of subject. Therefore, a cosmetic or pharmaceutical composition containing the carrier for an insoluble active substance can maximize the effect of the active substance.

19 Claims, 6 Drawing Sheets

(56) References Cited

FOREIGN PATENT DOCUMENTS

| KR | 10-0648535 B1 | 11/2006 |
| KR | 10-0921959 B1 | 10/2009 |
| KR | 10-2012-0114730 A | 10/2012 |
| KR | 10-2014-0070430 A | 6/2014 |
| KR | 10-2015-0000112 A | 1/2015 |
| KR | 10-2016-0065328 A | 6/2016 |
| KR | 10-1694987 B1 | 1/2017 |
| KR | 10-1808163 B1 | 12/2017 |
| WO | 2006/018024 * | 2/2006 |
| WO | 2016/109880 * | 7/2016 |
| WO | 2020/058892 * | 3/2020 |

OTHER PUBLICATIONS

Scognamiglio, I et al International Journal of Pharmaceutics, vol. 440, issue 2, Jan. 20, 2013, pp. 179-187.*
Huang, Y et al Journal of Drug Targeting, 19 (8), pp. 709-718, 2011.*
Pena-Rodriguez, E. et al, Pharmaceutics, 12, pp. 1-14, 1999.*
Sc0gnamiglio, I et al, International Journal of Pharmaceutics, 440, issue 2, Jan. 20, 2013, pp. 179-187.*
Iqrar Ali Alvia et al., "Comparative study of transfersomes, liposomes, and niosomes for topical delivery of 5-fluorouracil to skin cancer cells: preparation, characterization, in-vitro release, and cytotoxicity analysis", Anti-Cancer Drugs, 2011, pp. 774-782, vol. 22, No. 8.

* cited by examiner

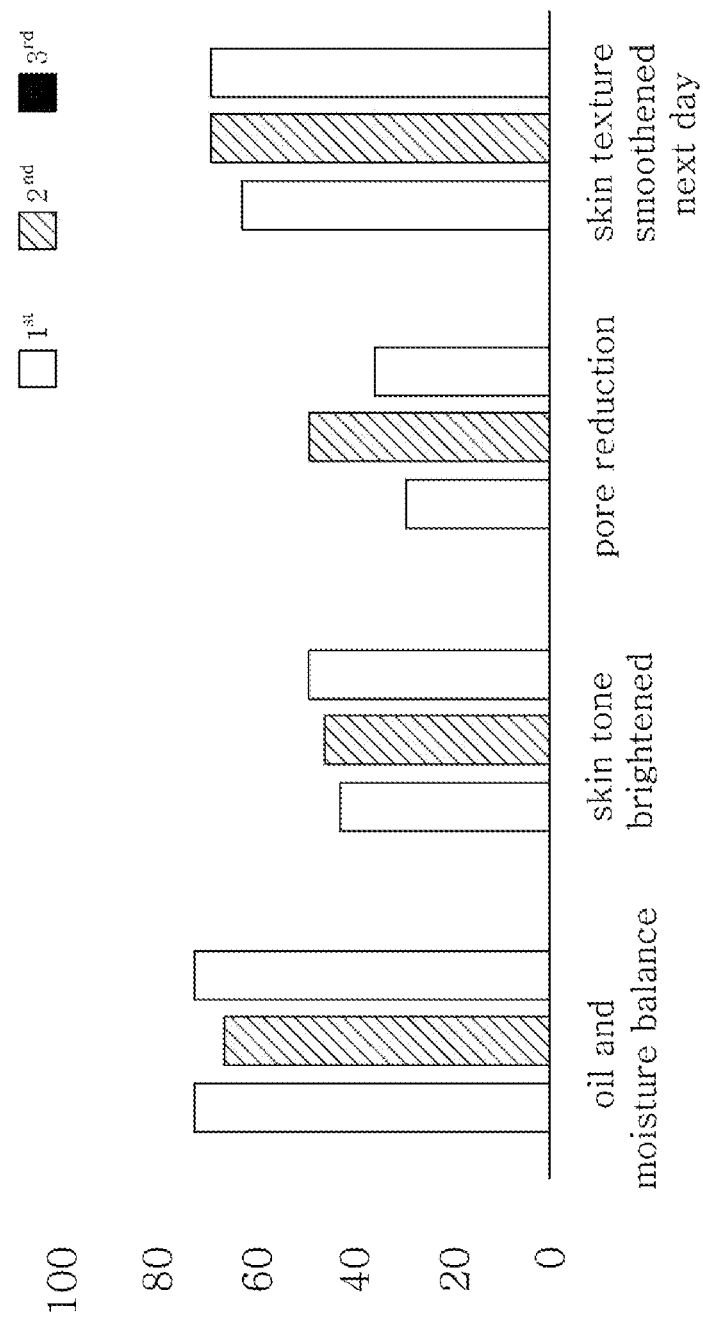

INSOLUBLE ACTIVE SUBSTANCE CARRIER COMPRISING TRANSFERSOME

CROSS REFERENCE TO RELATED APPLICATION

The present application claims priority to Korean Patent Application No. 10-2021-0022078, filed on Feb. 18, 2021, the entire contents of which is incorporated herein for all purposes by this reference.

BACKGROUND

Field

The present disclosure describes a carrier capable of stabilizing insoluble active substance.

Description of the Related Art

When a skin external formulation comprises an active substance that is difficult to penetrate into a stratum corneum, a synthetic surfactant and the like has been used in the cosmetic industry or pharmaceutical industry to promote skin absorption of the active substance. Alternatively, a method of increasing the skin permeability of the active substance by using polymer nanoparticles using a synthetic polymer such as polyethylene glycol or liposomes comprising an amphiphilic compound and a co-stabilizer cholesterol is widely used. However, when such method is applied to insoluble active substances such as phytosterol that do not dissolve well in water, the active substances are precipitated immediately upon manufacture so that there are difficulties in stabilization. Thus, there is a need for developing a carrier capable of effectively stabilizing the insoluble active substances.

SUMMARY

In one aspect, the problem to be solved by the present disclosure is to provide a carrier capable of stabilizing an insoluble active substance and promoting absorption of the insoluble active substance in the body.

In one aspect, the problem to be solved by the present disclosure is to provide a composition comprising a carrier capable of stabilizing an insoluble active substance and promoting absorption of the insoluble active substance in the body.

In one aspect, the present disclosure provides a carrier for an insoluble active substance comprising transfersome comprising a bilayer structure having a phospholipid and a single chain nonionic surfactant, and the phospholipid is a saturated phospholipid, and a hydrophic tail of the phospholipid and the hydrophobic tail of the single chain nonionic surfactant have different carbon numbers from each other.

In one aspect, the present disclosure provides a composition comprising an insoluble active substance and a carrier for the insoluble active substance.

In one aspect, the present disclosure provides a carrier for an insoluble active substance. The carrier according to an embodiment of the present disclosure can stabilize the insoluble active substance in a high content, and has a particle size about 10 times or more smaller than that of a liposome. Therefore, with the use of the carrier of the present disclosure, the absorption of the insoluble active substance into the body can be promoted. Therefore, a cosmetic or pharmaceutical composition comprising the carrier for an insoluble active substance of the present disclosure can maximize the effect of the active substance.

BRIEF DESCRIPTION OF THE DRAWINGS

FIG. 8 is a diagram showing an additional effect evaluation result of Preparation Example 2 according to an embodiment of the present disclosure.

DETAILED DESCRIPTION

Figure 1:
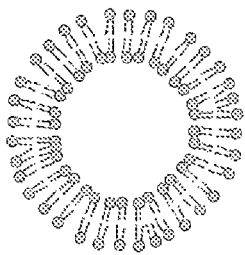
FIG. 1 is a schematic diagram of a form of a liposome, which is a comparative example of the present disclosure.

Hereinafter, embodiments of the present application will be described in more detail with reference to the accompanying drawings. However, the technology disclosed in the present application is not limited to the embodiments described herein and may be embodied in other forms. However, the embodiments introduced herein are provided so that the disclosed content may be thorough and complete, and the spirit of the present application may be sufficiently conveyed to those skilled in the art. In order to clearly express each component in the drawing, the size of the component, such as width or thickness, is slightly enlarged. In addition, although only some of the components are illustrated for convenience of description, those skilled in the art will be able to easily grasp the remaining parts of the components. Those of ordinary skill in the art will be able to implement the spirit of the present application in various other forms within the scope that does not depart from the technical spirit of the present application.

In the specification, a singular expression includes a plural expression unless the context clearly dictates otherwise. In the present application, terms such as "comprises", "contains" or "have" are intended to designate that a feature, number, step, operation, component, or combination thereof described in the specification is present, and the possibility of the presence or addition of one or other features, numbers, steps, operations, components or combinations thereof is not excluded.

An embodiment of the present disclosure provides a carrier for an insoluble active substance comprising a transfersome.

In particular, the present disclosure may comprise a transfersome comprising a bilayer structure having a phospholipid and a single chain nonionic surfactant, the phospholipid may be a saturated phospholipid, and a hydrophobic tail of the phospholipid and a hydrophobic tail of the single chain nonionic surfactant may have different carbon numbers from each other.

As used herein, the term "hydrophobic tail" refers to a major tail of the phospholipid or single chain nonionic surfactant, and the major tail refers to a major fatty acid of the tail of the phospholipid or single chain nonionic surfactant.

As used herein, the term "transfersome" comprises two or more of amphiphilic substances having a hydrophilic head and a hydrophobic tail, and refers to a structure comprising the bilayer structure in which the respective hydrophobic tails of the two or more of amphiphilic substances are arranged by intersecting regularly or irregularly. The transfersome may have various properties depending on the type, size, manufacturing method, etc. of the amphiphilic substances comprised.

Figure 2:
FIG. 2 is a schematic diagram of a spherical shape of a transfersome according to an embodiment of the present disclosure.
Figure 3:
FIG. 3 is a schematic diagram of a discoidal shape of a transfersome according to an embodiment of the present disclosure.

The accompanying FIGS. 1 to 3 show exemplary forms of a liposome (FIG. 1), which is a conventional carrier for an active substance, and transfersomes (FIGS. 2 and 3) of the present disclosure, respectively. Referring to FIGS. 1 and 2, both the liposome and transfersome are common in that they can entrap a hydrophilic substance in an aqueous compartment, which is the core of each structure, and entrap an insoluble substance that is poorly soluble in water, in the space within the bilayer structure. However, in the case of liposome, since the phospholipid, which is a double chain amphiphilic substance, constitutes the bilayer structure, there is very little space for entrapping the hydrophobic substance in the bilayer structure. On the other hand, the transfersome according to an embodiment of the present disclosure forms the bilayer structure in which the phospholipid having hydrophobic tails having different carbon numbers, as two or more of amphiphilic substances, and the single chain nonionic surfactants intersect regularly or irregularly. Due to the difference in the lengths of the hydrophobic tails and the single chain of the nonionic surfactant, a sufficient space can be formed to entrap the insoluble substance in a high content in the bilayer structure.

In the present specification, the term "insoluble substance" refers to a substance having low solubility in water, for example, the insoluble substance may be an oil-soluble, hydrophobic or water-insoluble substance. As used herein, the term "efficacy substance" refers to a substance having a useful efficacy on the skin or body. In particular, the insoluble active substance according to an embodiment of the present disclosure is not limited in its type, as long as it can be entrapped in the bilayer structure of the transfersome according to an embodiment of the present disclosure, and all may be comprised in the transfersome. For example, the insoluble active substance may comprise one or more selected from the group consisting of phytosterol, phytosphingosine, salicyloyl phytosphingosine, thymol trimethoxycinnamate, ceramide NP, ceramide NS, ceramide AS, ceramide AP, ceramide EOP, hydroxypropyl bislauramide MEA, hydroxypropyl bispalmitamide MEA, asiaticoside, asiatic acid, madecassic acid, and ferulic acid. For example, phytosterol is also referred to as beta-sitosterol, and although it is an active substance useful as a soothing substance for skin troubles, its melting point is 140° C., which is insoluble, so there is a problem that it is easily precipitated even when comprised through a conventional composition or a conventional liposome-type delivery system. However, when entrapped in the carrier according to an embodiment of the present disclosure, it is possible to provide a formulation having excellent stability even when a high content of phytosterol is entrapped.

As an embodiment, the difference in carbon numbers of the hydrophobic tail of the phospholipid and the hydrophobic tail of the single chain nonionic surfactant comprised in the transfersome is not limited to the type of the phospholipid and single chain nonionic surfactant comprised in the transfersome, and all cases in which the number of carbon atoms of the hydrophobic tail of the phospholipid, that is, the length of the hydrophobic tail of the phospholipid, is longer or shorter than that of the hydrophobic tail of the single chain nonionic surfactant are comprised. For example, the difference in carbon numbers between the hydrophobic tail of the phospholipid and the hydrophobic tail of the single chain nonionic surfactant may be 3 or more. More specifically, the difference in carbon numbers between the hydrophobic tail of the phospholipid and the hydrophobic tail of the single chain nonionic surfactant may be 3 or more, 4 or more, 5 or more, 6 or more, 7 or more, 8 or more, 9 or more, 10 or more, 11 or more, or 12 or more. More particularly, the difference in carbon numbers between the hydrophobic tail of the phospholipid and the hydrophobic tail of the single chain nonionic surfactant may be 13 or less, 12 or less, 11 or less, 10 or less, 9 or less, or 8 or less. If the difference in carbon numbers is less than 3, the difference in the lengths of the hydrophobic tail of the phospholipid and the hydrophobic tail of the single chain nonionic surfactant is not large, so the entrapment rate of the insoluble active substance is low, and if the difference in carbon numbers is more than 13, the particle size of the transfersome carrier is increased or the transfersome carrier itself is not formed, so that the skin absorption efficiency may be reduced, and the entrapment rate or stability of the active substance may be reduced.

As an embodiment, the type of the phospholipid is not limited as long as it is a saturated phospholipid of an amphipathic property having a hydrophilic head and a hydrophobic tail. As an embodiment, the phospholipid may have a length of 10 to 26 carbon atoms in the hydrophobic tail. Particularly, the single chain nonionic surfactant may have a length of 10, 11, 12, 13, 14, 15, 16, 17, 18, 19, 20, 21, 22, 23, 24, 25, or 26 carbon atoms in the hydrophobic tail. In particular, the phospholipid may comprise one or more selected from the group consisting of hydrogenated lecithin, hydrogenated phosphatidylcholine, phosphatidylinositol, phosphatidylethanolamine, and phosphatidylglycerol. Here, the "hydrogenated lecithin" refers to a hydrogenated product of lecithin, and the "hydrogenated phosphatidylcholine" refers to a hydrogenated product of phosphatidylcholine. As an embodiment, the carrier for an insoluble active substance may comprise the phospholipid in an amount of 0.01% by weight to 50% by weight based on the total weight of the carrier. In one embodiment, the carrier for an insoluble active substance may comprise the phospholipid in an amount of 0.01% by weight or more, 5% by weight or more, 10% by weight or more, 15% by weight or more, 20% by weight or more, 25% by weight or more, 30% by weight or more, 35% by weight or more, 40% by weight or more, or 45% by weight or more, based on the total weight of the carrier. In one embodiment, the carrier for an insoluble active substance may comprise the phospholipid in an amount of 50% by weight or less, 45% by weight or less, 40% by weight or less, 35% by weight or less, 30% by weight or less, 25% by weight or less, 20% by weight or less, 15% by weight or less, 10% by weight or less, 5% by weight or less, 1% by weight or less, or 0.1% by weight or less, based on the total weight of the carrier. If the content of the phospholipid in the carrier is less than 0.01% by weight, the transfersome carrier cannot be formed by combining with the single chain nonionic surfactant, and if the content of the phospholipid exceeds 50% by weight, problems such as, impediment to forming the transfersome carrier, increase in unit price, deterioration in feeling of use, reduced skin absorption effect, decrease in the entrapment rate of active substance, and stability problem, and the like may occur.

In one embodiment, the single chain nonionic surfactant is not limited to a certain type as long as it can form the transfersome together with the phospholipid, for example, it may comprise one or more selected from the group consisting of PPG-based, PEG-based, polysorbate-based, polyglyceryl-based, saccharide-based and biological surfactants. In one embodiment, the single chain nonionic surfactant may have a length of 8 to 30 carbon atoms in the hydrophobic tail. Particularly, the single chain nonionic surfactant may have a length of 8, 9, 10, 11, 12, 13, 14, 15, 16, 17, 18, 19, 20, 21, 22, 23, 24, 25, 26, 27, 28, 29 or 30 carbon atoms in the hydrophobic tail. More particularly, the single chain nonionic surfactant may comprise one or more selected from the group consisting of is PPG-13-decyltetradeceth-24, PEG-60 hydrogenated castor oil, PEG-40 hydrogenated castor oil, polysorbate 20, PPG polyglyceryl-6 caprylate, polyglyceryl-10 stearate, polyglyceryl-10 laurate, isotrideceth-9, sucrose stearate, sodium surfactin, nonadecanoyl nitrilo triacetic acid, arachidonoyl nitrilo triacetic acid, pentacosanoyl nitrilo triacetic acid, and pentacosanoyl nitrilo triacetic acid. In one embodiment, the carrier for an insoluble active substance may comprise the single chain nonionic surfactant in an amount of 0.01% by weight to 95% by weight based on the total weight of the carrier. In one embodiment, the carrier for an insoluble active substance may comprise, based on the total weight of the carrier, the single chain nonionic surfactant in an amount of 0.01% by weight or more, 25% by weight or more, 30% by weight or more, 35% by weight or more, 40% by weight or more, 45% by weight or more, 50% by weight or more, 55% by weight or more, 60% by weight or more, 65% by weight or more, 70% by weight or more, 75% by weight or more, 80% by weight or more, 85% by weight or more, or 90% by weight or more. In one embodiment, the carrier for an insoluble active substance may comprise, based on the total weight of the carrier, the single chain nonionic surfactant in an amount of 95% by weight or less, 90% by weight or less, 85% by weight or less, 80% by weight or less, 75% by weight or less, 70% by weight or less, 65% by weight or less, 60% by weight or less, 55% by weight or less, 50% by weight or less, 45% by weight or less, 40% by weight or less, 35% by weight or less, 30% by weight or less, or 25% by weight or less. If the content of the single chain nonionic surfactant in the carrier is less than 0.01% by weight, the transfersome carrier cannot be formed by combining the single chain nonionic surfactant with the phospholipid having a double chain. If the content of the single chain nonionic surfactant is greater than 95% by weight, problems such as impediment to forming the transfersome carrier, increase in unit cost, deterioration in feeling of use, reduced skin absorption effect, decrease in the entrapment rate of active substance, stability problem, and the like may occur.

In one embodiment, the weight ratio of the phospholipid and the single chain nonionic surfactant may be 1:1 or more. For example, the weight ratio of the phospholipid and the single chain nonionic surfactant may be 1:1 or more, 1:2 or more, 1:3 or more, 1:4 or more, 1:5 or more, 1:6 or more, 1:7 or more, 1:8 or more, 1:9 or more, 1:10 or more, 1:11 or more, 1:12 or more, 1:13 or more, 1:14 or more, 1:15 or more, 1:16 or more, 11:17 or more, 1:18 or more or 1:19 or more. In addition, for example, the weight ratio of the phospholipid and the single chain nonionic surfactant may be 1:20 or less, 1:19 or less, 1:18 or less, 1:17 or less, 1:16 or less, 1:15 or less, 1:14 or less, 1:13 or less, 1:12 or less, 1:11 or less, 1:10 or less, 1:9 or less, 1:8 or less, 1:7 or less, 1:6 or less, 1:5 or less, 1:4 or less, 1:3 or less or 1:2 or less. More particularly, the weight ratio of the phospholipid and the single chain nonionic surfactant may be 1:1 to 20. If the weight ratio is out of the above range, the transfersome carrier may not be formed, so that the entrapment rate of the active substance may be reduced or the stability may be reduced.

In one embodiment, the carrier for an insoluble active substance may comprise the transfersome comprising the bilayer structure having the phospholipid and two or more single chain nonionic surfactants. For example, the carrier for an insoluble active substance may comprise two, three, four or more single chain nonionic surfactants. In this case, as an embodiment, the hydrophobic tail of one or more single chain nonionic surfactants among the two or more single chain nonionic surfactants may comprise a different number of carbon atoms from the hydrophobic tail of the phospholipid.

In addition, in one embodiment, the two or more single chain nonionic surfactants may have different hydrophile-lipophile-balance (HLB) values from each other. For example, the difference in the HLB values between the two or more single chain nonionic surfactants may be 1.5 or more. If the difference in HLB values of the two or more single chain nonionic surfactants is less than 1.5, the difference in the entrapment rate of the insoluble active substance according to the difference in HLB values is insignificant. Particularly, the difference in HLB values between the two or more single chain nonionic surfactants may be 1.5 to 18. More particularly, the difference in HLB values of the two or more single chain nonionic surfactants may be 1.5 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or 17 or more. More particularly, the difference in HLB values of the two or more single chain nonionic surfactants may be 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, 3 or less, or 2 or less.

In addition, in one embodiment, the two or more single chain nonionic surfactants may have different structures from each other. For example, the structure of the single chain nonionic surfactant may be a linear, nonlinear, branched or cyclic structure.

In one embodiment, the particle shape of the carrier for an insoluble active substance is not be limited, and may be any as long as the bilayer structure having the phospholipid and the single chain nonionic surfactant is formed. For example, the particle shape of the carrier for an insoluble active substance may be a spherical shape, a disk shape, a crushed sphere, a cylinder shape, and the like.

In one embodiment, the particle size of the carrier for an insoluble active substance may be 5 to 20 nm, but is not limited thereto. In the present specification, the particle size refers to a size (nm) corresponding to a main peak (peak) based on the number of particles observed for each size. Particularly, the particle size refers to the largest diameter of a corresponding particle, and refers to the size of at least 90% or more of the carrier particles distributed in the structure, carrier or composition. Particularly, the particle size of the carrier may refer to the largest diameters of at least 90% or more, 91% or more, 92% or more, 93% or more, 94% or more, 95% or more, 96% or more, 97% or more, 98% or more, or 99% or more of the carriers comprised in the composition. In addition, in one embodiment, the particles of the carrier for an insoluble active substance may have a uniform size. Particularly, the particle sizes of at least 90% or more, 91% or more, 92% or more, 93% or more, 94% or more, 95% or more, 96% or more, 97% or more, 98% or more, or 99% or more of the carrier for an insoluble active substance comprised in the composition may be 5 to 20 nm. Particularly, the particle size of the carrier may be 5 nm or more, 6 nm or more, 7 nm or more, 8 nm or more, 9 nm or more, 10 nm or more, 11 nm or more, 12 nm or more, 13 nm or more, 14 nm or more, 15 nm or more, 16 nm or more, 17 nm or more, 18 nm or more, or 19 nm or more. Particularly, the particle size of the carrier may be 20 nm or less, 19 nm or less, 18 nm or less, 17 nm or less, 16 nm or less, 15 nm or less, 14 nm or less, 13 nm or less, 12 nm or less, 11 nm or less, 10 nm or less or less, 9 nm or less, 8 nm or less, 7 nm or less, or 6 nm or less. Since the carrier for an insoluble active substance according to embodiments of the present disclosure has the particle size of about 10 times or more smaller than that of the conventional liposome, it can be absorbed more effectively when applied to the skin.

In one embodiment, the carrier may further comprise oil in the bilayer structure. In one embodiment, the oil can more stabilize the insoluble active substance within the bilayer structure. The type of the oil is not limited, and any oil commonly used in the art may be used. For example, the oil may have compatibility with the nonionic surfactant, and particularly, the oil may comprise one or more of a hydrocarbon-based oil and a silicone-based oil. More particularly, the oil may comprise one or more selected from the group consisting of squalane, caprylic/capric triglyceride, cetyl ethylhexanoate, dibutyl adipate, neopentyl glycol diheptanoate, butylenes glycol dicaprylate/dicaprate, phenyl trimethicone, methyl trimethicone, cyclopentasiloxane, cyclohexasiloxane, caprylyl methicone, dimethicone, and trisiloxane. In one embodiment, the oil may be comprised in an amount of 0.001% by weight to 25% by weight based on the total weight of the carrier. Particularly, the oil may be comprised in an amount of 0.001% by weight or more, 0.01% by weight or more, 0.05% by weight or more, 0.1% by weight or more, 0.5% by weight or more, 1% by weight or more, 5% by weight or more, 10% by weight or more, 15% by weight or more, or 20% by weight or more. In particular, the oil may be comprised in an amount of 25% by weight or less, 20% by weight or less, 15% by weight or less, 10% by weight or less, 5% by weight or less, 1% by weight or less, 0.5% by weight or less, 0.1% by weight or less, or 0.05% by weight or less. When the oil is comprised in excess of 25% by weight, impediment to forming the transfersome carrier, increase in a particle size, increase in turbidity, and reduced stability may occur.

According to an embodiment of the present disclosure, the carrier for an insoluble active substance has an excellent entrapment rate of the insoluble active substance and has a small particle size, thereby effectively stabilizing the high content of the insoluble active substance without precipitation and gelling.

In one embodiment, the present disclosure may provide a composition comprising the above-described carrier for an insoluble active substance and the insoluble active substance.

Another embodiment may provide the use of the transfersome as the carrier for an insoluble active substance for use in the preparation of a composition comprising the insoluble active substance. Another embodiment may provide a method for delivering an insoluble active substance into the body, which comprises entrapping an effective amount of the insoluble active substance in the carrier for the insoluble substance comprising the transfersome. Another embodiment may provide the composition comprising the insoluble active substance with the transfersome as the carrier for the insoluble active substance for facilitating the delivery of the insoluble active substance comprised in the composition. In addition, it is possible to provide the use of the transfersome as the carrier for the insoluble active substance.

In one embodiment, the insoluble active substance may be comprised in an amount of 0.001% by weight to 10% by weight based on the total weight of the composition. If the insoluble active substance is comprised in less than 0.001% by weight, the desired efficacy of the insoluble active substance may not be sufficiently exhibited. In one embodiment, if the insoluble active substance is comprised in excess of 10% by weight, there may be problems such as impediment to forming the transfersome carrier, increase in a particle size, increase in turbidity, and reduced stability. Particularly, the insoluble active substance may be comprised in an amount of 0.001% by weight or more, 0.01% by weight or more, 0.02% by weight or more, 0.03% by weight or more, 0.04% by weight or more, 0.05% by weight or more, 0.06% by weight or more, 0.07% by weight or more, 0.08% by weight or more, 0.09% by weight or more, 0.1% by weight or more, 0.2% by weight or more, 0.3% by weight or more, 0.4% by weight or more, 0.5% by weight or more, 0.6% by weight or more, 0.7% by weight or more, 0.8% by weight or more, 0.9% by weight or more, 1% by weight or more, 2% by weight or more, 3% by weight or more, 4% by weight or more, 5% by weight or more, 6% by weight or more, 7% by weight or more, 8% by weight or more, 9% by weight or more or 9.99% by weight or more, based on the total weight of the composition. In one embodiment, the insoluble active substance may be comprised in an amount of 10% by weight or less, 9% by weight or less, 8% by weight or less, 7% by weight or less, 6% by weight or less, 5% by weight or less, 4% by weight or less, 3% by weight or less, 2% by weight or less, 1% by weight or less, 0.9% by weight or less, 0.8% by weight or less, 0.7% by weight or less, 0.6% by weight or less, 0.5% by weight or less, 0.4% by weight or less, 0.3% by weight or less, 0.2% by weight or less, 0.1% by weight or less, 0.09% by weight or less, 0.08% by weight or less, 0.07% by weight or less, 0.06% by weight or less, 0.05% by weight or less, 0.04% by weight or less, 0.03% by weight or less, 0.02% by weight or less, or 0.01% by weight or less, based on the total weight of the composition.

In one embodiment, the total weight ratio of the carrier for an insoluble active substance to the total weight of the insoluble active substance comprised in the composition may be 1:1 to 100. If the ratio exceeds the above range, impediment to forming the transfersome carrier, increase in particle size, increase in turbidity, reduced stability, and reduced skin absorption effect may occur. Particularly, the total weight ratio of the carrier for an insoluble active substance to the total weight of the insoluble active substance may be 1:1 or more, 5 or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, or 95 or more. Particularly, the total weight ratio of the carrier for an insoluble active substance to the total weight of the insoluble active substance may be 1:100 or less, 95 or less, 90 or less, 85 or less, 80 or less, 75 or less, 70 or less, 65 or less, 60 or less, 55 or less, 50 or less, 45 or less, 40 or less, 35 or less, 30 or less, 25 or less, 20 or less, 15 or less, 10 or less, 5 or less, or 2 or less.

In one embodiment, the carrier for an insoluble active substance may further comprise oil in the bilayer structure, and the type of oil is as described above. In one embodiment, the oil comprised in the carrier for an insoluble active substance may be comprised in an amount of 0.01 to 10% by weight based on the total weight of the composition, but is not limited thereto. In particular, the oil may be comprised in an amount of 0.01% by weight or more, 0.1% by weight or more, 1% by weight or more, 2% by weight or more, 3% by weight or more, 4% by weight or more, 5% by weight or more, 6% by weight or more, 7% by weight or more, 8% by weight or more, or 9% by weight or more, based on the total weight of the composition. Particularly, the oil may be comprised in an amount of 10% by weight or less, 9% by weight or less, 8% by weight or less, 7% by weight or less, 6% by weight or less, 5% by weight or less, 4% by weight or less, 3% by weight or less, 2% by weight or less, 1% by weight or less, or 0.1% or less, based on the total weight of the composition. If the oil is comprised in an amount of less than 0.01% by weight, the problems such as reduced solubility of the insoluble active substance, impediment to forming the transfersome carrier, increase in particle size, increase in turbidity, and reduced stability may occur, and if the oil is comprised in an amount of more than 10% by weight, problems such as impediment to forming the transfersome carrier, increase in particle size, increase in turbidity, and reduced stability may occur.

In one embodiment, the dosage or amount of dose administered to the body of the carrier for an insoluble active substance in which the insoluble active substance is entrapped may be 50 mg/kg/day to 10000 mg/kg/day. The dosage may vary depending on the age, sex, weight, and specific disease or pathological condition of a subject, the severity of the disease or pathology, the route of administration, and the like, and the dosage determination based on these factors is within the level of those skilled in the art. For example, the dosage may be 50 mg/kg/day or more, 100 mg/kg/day or more, 150 mg/kg/day or more, 200 mg/kg/day or more, 250 mg/kg/day or more, 300 mg/kg/day or more, 350 mg/kg/day or more, 400 mg/kg/day or more, 450 mg/kg/day or more, 500 mg/kg/day or more, 550 mg/kg/day or more, 600 mg/kg/day or more, 650 mg/kg/day or more, 700 mg/kg/day or more, 750 mg/kg/day or more, 800 mg/kg/day or more, 850 mg/kg/day or more, 900 mg/kg/day or more or 1000 mg/kg/day or more. In addition, the dosage may be, for example, 10 g/kg/day or less, 5000 mg/kg/day or less, 4500 mg/kg/day or less, 4000 mg/kg/day or less, 3500 mg/kg/day or less, 3000 mg/kg/day or less, 2500 mg/kg/day or less, 2000 mg/kg/day or less, 1500 mg/kg/day or less, 1000 mg/kg/day or less, or 500 mg/kg/day or less, but the dosage is not intended to limit the scope of this specification in any way.

The composition according to an embodiment of the present disclosure may be an external preparation for skin.

The composition according to embodiments of the present disclosure may be a cosmetic composition.

In one embodiment, a cosmetic composition according to the present disclosure may be formulated comprising a cosmetically or dermatologically acceptable medium or base. This may be any formulation suitable for topical application, for example, in the form of solution, gel, solid, dough anhydride, emulsion obtained by dispersing an oily phase in an aqueous phase, suspension, microemulsion, microcapsule, microgranule, ionic (liposomes) nonionic vesicle dispersion and film, or in the form of cream, skin lotion, milky lotion, powder, ointment, spray or conceal stink. The composition may also be used in the form of a foam or an aerosol composition further comprising a compressed propellant. These compositions may be prepared according to conventional methods in the art. In one embodiment, the cosmetic composition according to the present disclosure may preferably comprise other components capable of giving a synergistic effect to a main effect together with the active ingredient within a range that does not impair the main effect, and in addition to the active substance of the present disclosure, other ingredients may be appropriately selected and formulated by those skilled in the art without difficulty depending on the formulation or purpose of use of other cosmetic compositions. In addition, in one embodiment, the cosmetic composition of the present disclosure may comprise other components that are usually blended into the cosmetic composition, if necessary, in addition to the above components. For example, there are thickeners, neutralizers, antioxidants, humectants, emollients, organic and inorganic pigments, organic powders, UV absorbers, preservatives, disinfectants, other functional raw materials, pH adjusters, alcohols, colorants, fragrances, blood circulation promoters, cooling agents, anti-perspiration agents, purified water, etc. Other compounding substances that may be comprised in the cosmetic composition of the present disclosure are not limited thereto, and the compounding amount of the components is possible within a range that does not impair the purpose and effect of the present disclosure.

The composition according to an embodiment of the present disclosure may be a pharmaceutical composition. The pharmaceutical composition may further comprise pharmaceutical additives such as preservatives, stabilizers, hydrating agents or emulsification promoters, salts and/or buffers for osmotic control, and other therapeutically useful substances. In one embodiment, the pharmaceutical composition may be a parenteral administration agent, and the parenteral administration agent may be a rectal, topical, subcutaneous, or transdermal dosage form. For example, it may be in the form of injections, drops, ointments, lotions, gels, creams, sprays, suspensions, emulsions, suppositories, patches, etc., but is not limited thereto. In one embodiment, the dosage of the pharmaceutical composition may vary depend on the age, sex, and weight of a subject to be treated, the particular disease to be treated or pathological conditions thereof, the severity of the disease or pathological conditions, administration route, and discretion of a prescriber. The dosage determination based on these factors is within the level of those skilled in the art. For example, the dosage may be 50 mg/kg/day or more or 1000 mg/kg/day or more, and may be 10 g/kg/day or less or 5000 mg/kg/day or less, but the above dosage does not limit the scope of the present specification in any way.

Hereinafter, the present disclosure will be described in detail with reference to Examples, Comparative Examples and Test Examples. These are only presented by way of example to explain the present disclosure in more detail, and it will be apparent to those skilled in the art that the scope of the present disclosure is not limited by these Examples, Comparative Examples and Test Examples.

Comparative Example

As a comparative example of the present disclosure, a composition comprising liposomes, which is a carrier for an active substance, was prepared. Particularly, according to a conventional method for preparing a composition in the art, oil was added into the aqueous phase composed of the components except for oil in the composition shown in Table 1 below, and liposome was prepared through homomixing, azimixing, and heating process.

TABLE 1

| Components | | Comparative Example |
|---|---|---|
| Phospholipid | Hydrogenated lecithin | 0.3 |
| | Hydrogenated phosphatidylcholine | 0.3 |
| Oil | Squalane | 1 |
| | Etc. | To 100 |

(% by weight)

Figure 4:
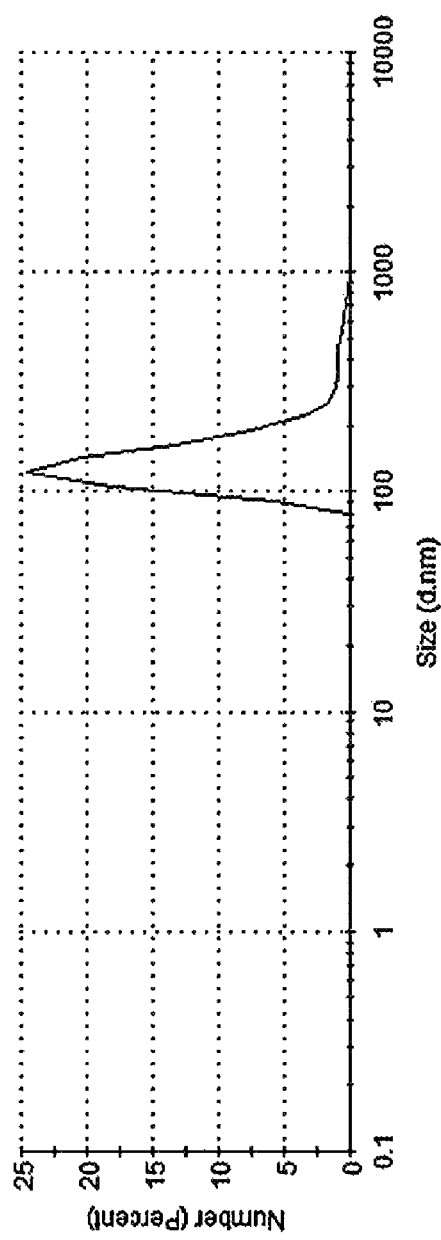
FIG. 4 is a diagram showing a particle size distribution of liposomes, which is a comparative example of the present disclosure, a main peak is shown in the size of 155 nm.

Then, the particle size distribution of the liposome of Comparative Example 1 was analyzed using a dynamic light scattering (DLS) particle size analyzer (product name: Zetasizer Nano ZS, manufacturer: Malvern Instruments, UK), and the results are shown in FIG. 4. In FIG. 4, the x-axis denotes the particle size (nm), and the y-axis denotes a percentage of the number of particles whose corresponding size is measured.

As a result, as shown in FIG. 4, the liposome showed a main peak at a particle size of 155 nm even though it did not comprise the active substance in the carrier.

Comparative Example 2

As another comparative example of the present disclosure, a composition comprising an insoluble active substance and a liposome that is the carrier for the insoluble active substance entrapped therein was prepared.

Particularly, according to a conventional method for preparing a composition in the art, the oil phase consisting of the insoluble active substance and oil in the composition of Table 2 below was added into the aqueous phase consisting of other components except for these, and Comparative Example 2 was prepared through homomixing, azimixing and heating process.

TABLE 2

| Component | | Comparative Example 2 |
|---|---|---|
| Phospholipid | Hydrogenated lecithin | 0.3 |
| | Hydrogenated phosphatidylcholine | 0.3 |
| Oil | Squalane | 1 |
| Insoluble active substance | Phytosterol (manufacturer: MMP Inc., product name: Phytosterol MM) | 0.5 |
| | Etc. | To 100 |

(% by weight)

As a result, in Comparative Example 2, it was confirmed that phytosterol was precipitated immediately after preparation, and the liposome carrier could not stabilize the insoluble active substance such as phytosterol.

Example 1

As an embodiment of the present disclosure, a composition comprising an insoluble active substance and a carrier for the insoluble active substance entrapped therein was prepared.

Particularly, according to a conventional method for preparing a composition in the art, the oil phase consisting of the insoluble active substance and oil in the composition of Table 3 was added into the aqueous phase consisting of other components except for these, and Example 1 was prepared through homomixing, azimixing and heating process.

TABLE 3

| Component | | HLB | Carbon number of hydrophobic tail | Exampe 1 |
|---|---|---|---|---|
| Phospholipid | Hydrogenated lecithin | 2-9 | C18 | 0.3 |
| | Hydrogenated phosphatidylcholine | 2-9 | C18 | 0.3 |
| Single chain nonionic surfactant | Polyglyceryl-10 Stearate | 17.5 | C18 | 1.0 |
| | Polyglyceryl-10 laurate | 17.2 | C12 | 0.6 |
| | Sucrose stearate | 15 | C18 | 1.3 |
| Oil | Squalane | | | 1 |
| Insoluble active substance | Phytosterol (manufacturer: MMP Inc., product name: Phytosterol MM) | | | 0.5 |
| | Etc. | | | To 100 |

(% by weight)

Figure 5:
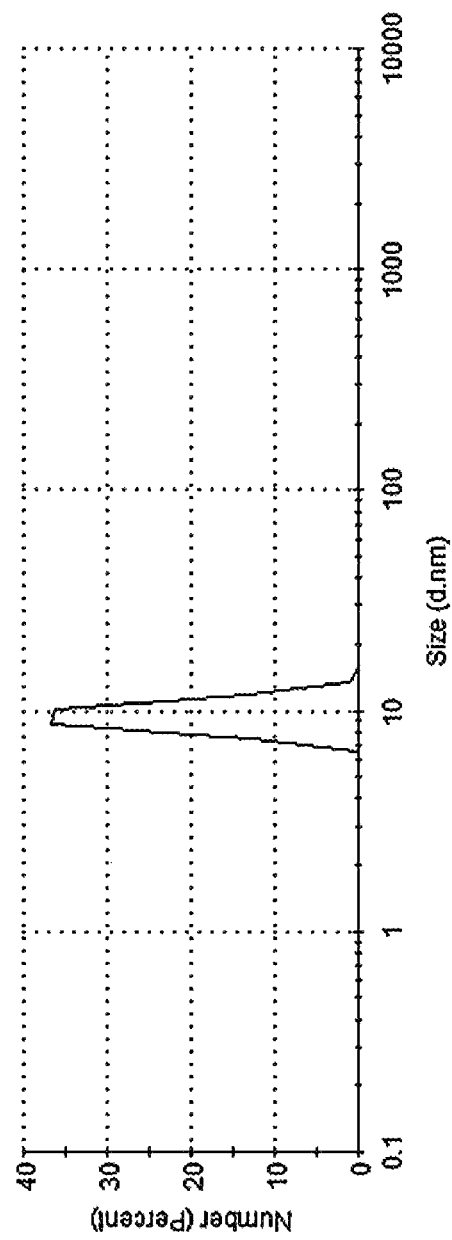
FIG. 5 is a diagram showing a particle size distribution of spherical transfersome, which is an embodiment of the present disclosure, a main peak is shown in the size of 9.5 nm.

As a result of analyzing the particle size distribution of the carrier comprised in the composition of Example 1 prepared above, as shown in FIG. 5, a main peak was shown at the particle size of 9.5 nm, and even though it comprised the insoluble active substance, it could be confirmed that the particle size of the carrier was significantly smaller than that of the liposome and was uniform. This means that the use of the carrier according to an embodiment of the present disclosure can increase the skin absorption of the insoluble active substance.

In addition, the stability of the composition was observed at room temperature, 30° C., 37° C., 45° C., 60° C., cycling (45° C., 12 hours to −15° C., 12 hours), frozen (−15° C.) and refrigerated (5° C.) for a total of one month. As a result of observing the stability, it was confirmed that the precipitation or gelling of phytosterol did not occur, and thus the stability was excellent. This means that the carrier according to an embodiment of the present disclosure effectively stabilizes the insoluble active substance.

Test Example 1

As examples and comparative examples of the present disclosure, according to a conventional method for preparing a composition in the art, the oil phase consisting of the oil or the oil and the insoluble active substance in the composition of Tables 4 and 5 below was added into the aqueous phase consisting of other components except for these, and the composition was prepared through homomixing, azimixing, and heating process.

Then, each prepared composition was subjected for observation at room temperature, 30° C., 37° C., 45° C., 60° C., cycling (45° C., 12 hours to −15° C., 12 hours), freezing (−15° C.) and refrigeration (5° C.) for a total of one month, and the observation results are shown in the table below. If the stability is good even after one month, it is indicated by ⊚, if it is good up to three weeks, ○, if it is good during manufacture, but precipitation or gelling occurs within 1 to 2 weeks, it is indicated by Δ, and if it precipitates immediately after preparation, it is indicated by X.

TABLE 4

| | Component | HLB | Carbon No. of hydrophobic tail | Example 1 | Example 2 | Example 3 | Example 4 | Example 5 |
|---|---|---|---|---|---|---|---|---|
| Phospholipid | Hydrogenated lecithin | 2-9 | C18 | 0.3 | 0.3 | 0.3 | 0.3 | 0.3 |
| | Hydrogenated phosphatidylcholine | 2-9 | C18 | 0.3 | 0.3 | 0.3 | 0.3 | 0.3 |
| | Lecithin | 2-9 | C18 | — | — | — | — | — |
| | phosphatidylcholine | 2~9 | C18 | — | — | — | — | — |
| Single chain nonionic surfactant | Polyglyceryl-10 Stearate | 17.5 | C18 | 1.0 | 1.0 | — | 1.3 | — |
| | Polyglyceryl-10 laurate | 17.2 | C12 | 0.6 | 0.6 | 1.6 | 1.6 | — |
| | Sucrose stearate | 15 | C18 | 1.3 | 1.0 | 1.3 | — | — |
| | Sodium Surfactin | 20 | C11 | — | 0.3 | — | — | — |
| | PPG-13-decyltetradeceth-24 | 10.7 | C14 | — | — | — | — | 2.9 |
| Oil | Squalane | — | — | 1 | 1 | 1 | 1 | 1 |
| Insoluble active substance | Phytosterol | — | — | 0.5 | 0.5 | 0.5 | 0.5 | 0.5 |
| Etc. | | | | To 100 | To 100 | To 100 | To 100 | To 100 |
| Stability | | | | ◎ | ◎ | ◎ | ○ | ○ |

(% by weight)

TABLE 5

| | Composition of invention | HLB | Carbon No. of hydrophobic tail | Comp Example 1 | Comp Example 2 | Comp Example 3 | Comp Example 4 | Comp Example 5 | Comp Example 6 | Comp Example 7 | Comp Example 8 | Comp Example 9 | Comp Example 10 |
|---|---|---|---|---|---|---|---|---|---|---|---|---|---|
| Phospholipid | Hydrogenated lecithin | 2-9 | C18 | 0.3 | 0.3 | — | — | — | — | — | — | — | 0.15 |
| | Hydrogenated phosphatidylcholine | 2-9 | C18 | 0.3 | 0.3 | — | — | — | — | — | — | — | 0.15 |
| | Lecithin | 2-9 | C18 | — | — | 0.3 | — | — | — | — | — | 0.6 | — |
| | phosphatidylcholine | 2-9 | C18 | — | — | 0.3 | — | — | — | — | — | — | 0.3 |
| Single chain nonionic surfactant | Polyglyceryl-10 Stearate | 17.5 | C18 | 1.3 | — | — | 1.3 | — | — | — | — | 1.3 | 1.3 |
| | Polyglyceryl-10 laurate | 17.2 | C12 | — | — | — | 1.6 | — | — | — | — | 1.6 | 1.6 |
| | Sucrose stearate | 15 | C18 | 1.6 | — | — | — | 2.9 | — | — | — | — | — |
| | Sodium Surfactin | 20 | C11 | — | — | — | — | — | — | — | — | — | — |
| | PPG-13-decyltetradeceth-24 | 10.7 | C14 | — | — | — | — | — | 2.9 | — | — | — | — |
| | PEG-60-Hydrogenated Castor Oil | 14 | C18 | — | — | — | — | — | — | 2.9 | — | — | — |
| | Polysorbate 80 | 15 | C18 | — | — | — | — | — | — | — | 2.9 | — | — |
| Oil | Squalane | | | 1 | 1 | 1 | 1 | 1 | 1 | 1 | 1 | 1 | 1 |
| Insoluble active substance | Phytosterol | | | 0.5 | 0.5 | 0.5 | 0.5 | 0.5 | 0.5 | 0.5 | 0.5 | 0.5 | 0.5 |
| Etc. | | | | To 100 | To 100 | To 100 | To 100 | To 100 | To 100 | To 100 | To 100 | To 100 | To 100 |
| Stability | | | | Δ | X | X | X | X | X | X | X | Δ | Δ |

(% by weight)

In all of Comparative Examples 2 to 8, in which the liposomes comprising only phospholipids or single chain nonionic surfactant were prepared, the insoluble active substances were precipitated immediately after preparation. In addition, in Comparative Example 1 with the same number of carbon atoms in the hydrophobic tail of the phospholipid and the hydrophobic tail of the single chain nonionic surfactant even in the form of the transfersome, and in Comparatives 9 and 10 comprising unsaturated phospholipids even if the number of carbon atoms in the hydrophobic tail of the phospholipid and the hydrophobic tail of the single chain nonionic surfactant are different, it was confirmed that the insoluble active substances were precipitated within 1 to 2 weeks after preparation. In addition, in Comparative Examples 9 and 10, discoloration or odor was occurred due to the unsaturated phospholipid. On the other hand, in Examples 1 to 5 according to an embodiment of the present disclosure, any precipitation or gelling was not observed for 3 weeks or more, and it can be confirmed that the insoluble active substance is effectively stabilized.

Test Example 2

As a composition according to an embodiment of the present disclosure, Preparation Example 1 (#232), which is a thickening formulation having the same composition as in Example 1, and, Preparation Example 2 (#260), which is a thickening formulation having the same composition as Example 1, except that phytosterol was comprised in an amount of 0.3% by weight, were prepared, respectively. It was confirmed as in the experiment below whether each of the carriers of the present disclosure could maximize the effect of the insoluble active instance by promoting the skin absorption of the insoluble active instance.

First, 50 women in their twenties between the ages of 20 and 30 who are currently concerned about their skin troubles (accompanied by skin troubles) were selected as an evaluation panel, and they were divided into two groups of 30 people each. Group 1 (30 people) was to use Preparation Example 1 (#232) on a part of the face on the first to sixth days, and on the whole face on the seventh day. Group (30 people) was to use Preparation Example 2 (#260) all over the face for seven days. After seven days, the advance for treating skin troubles was evaluated. In addition to the advance for treating skin troubles, an additional improvement effects of skin appearance such as the degree of improvement in skin texture, smoothness, gloss, and elasticity were also evaluated.

Figure 6:
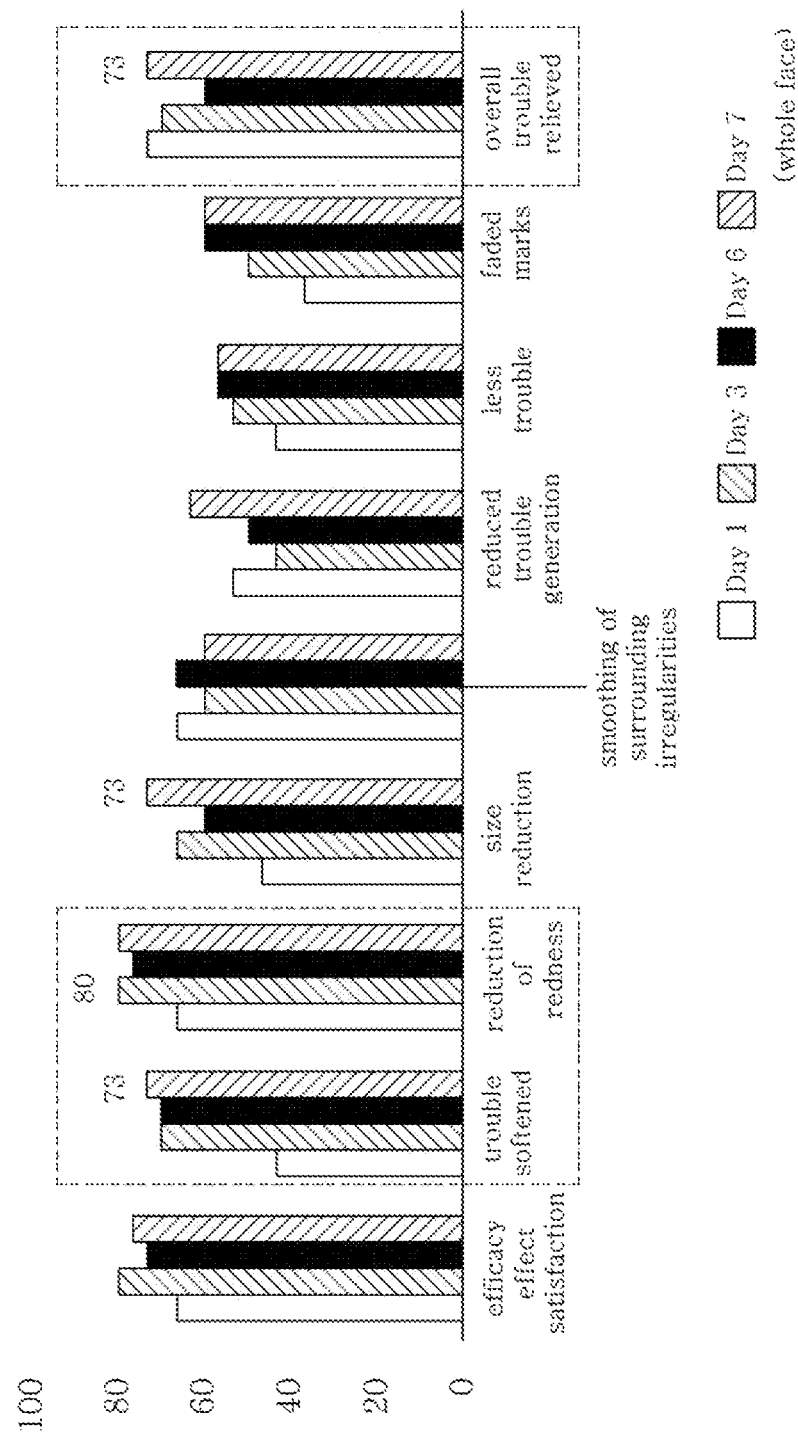
FIG. 6 is a diagram showing an efficacy satisfaction evaluation result of Preparation Example 1 according to an embodiment of the present disclosure.
Figure 7:
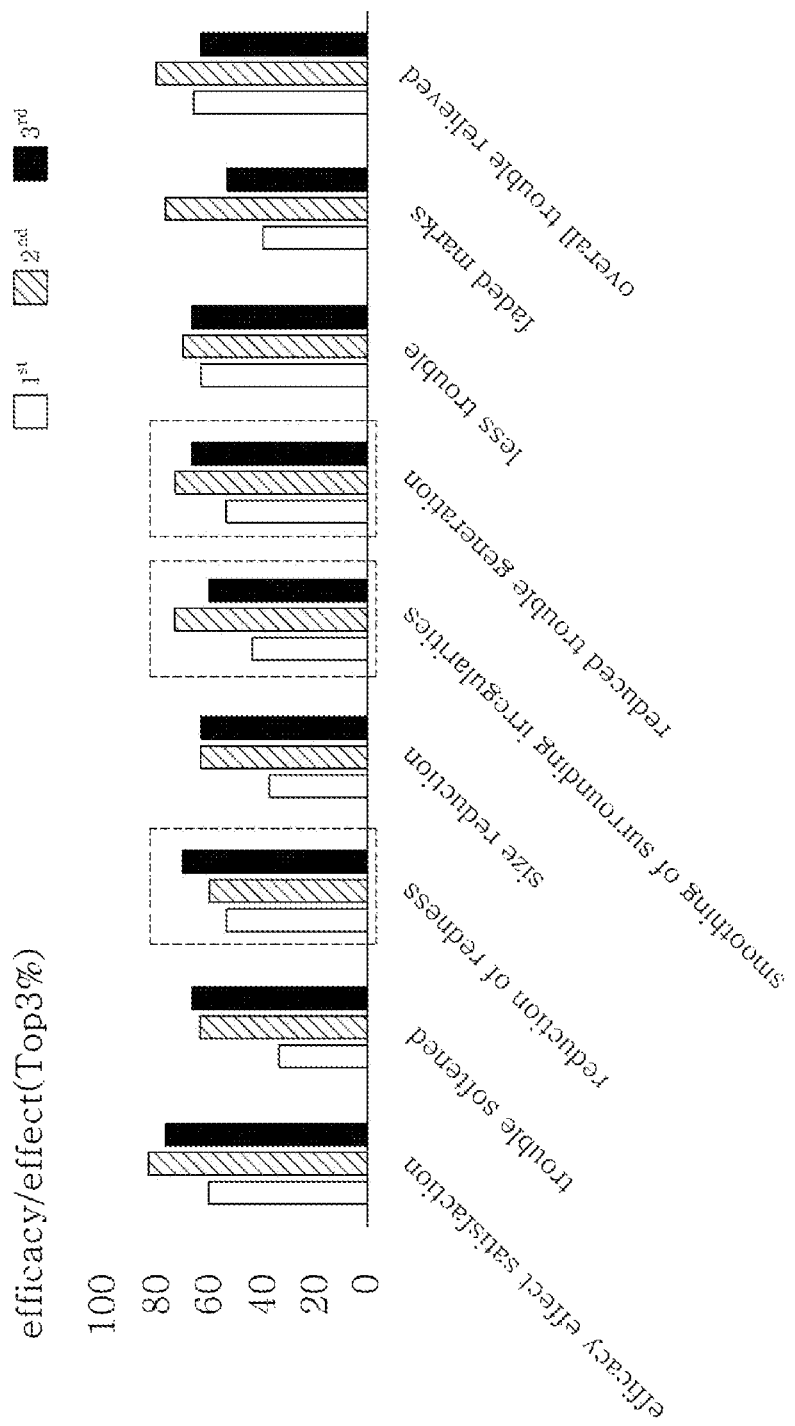
FIG. 7 is a diagram showing an efficacy and effect evaluation result of Preparation Example 2 according to an embodiment of the present disclosure.

As a result, it was found that Preparation Example 1 (#232) had an immediate skin soothing efficacy and/or effect as shown in FIG. 6, and the hardened problem area became softened, and the redness and size of the problem area were reduced. According to the number of days of use, it was evaluated that the redness and size reduction effect and the pain relief from the skin trouble were excellent on the first day, the progression of the skin trouble was slowed down on the third day, and the size and number of the skin troubles were decreased and the uneven area was treated on the seventh day. It was evaluated that Preparation Example 2 (#260) showed a redness relief effect as shown in FIG. 7, and as shown in FIG. 8, the skin became smooth and oil and moisture balance was controlled to prevent the occurrence of the skin troubles. Therefore, it can be confirmed that when using a composition in which the insoluble active substance is stabilized using the carrier for entrapping the insoluble active substance of the present disclosure, the insoluble active substance can be stably entrapped at a high content, resulting in excellent skin improvement effect.

The present disclosure may provide the following embodiments as exemplary embodiments.

A first embodiment provides a carrier for an insoluble active substance comprising a transfersome comprising a bilayer structure having a phospholipid and a single chain nonionic surfactant, wherein the phospholipid is a saturated phospholipid, and wherein the hydrophic tail of the phospholipid, and the hydrophobic tail of the single chain nonionic surfactant have different carbon numbers from each other.

The second embodiment provides the carrier of an insoluble active substance of the first embodiment in which the difference in carbon numbers between the hydrophobic tail of the phospholipid and the hydrophobic tail of the single chain nonionic surfactant is 3 or more.

The third embodiment provides the carrier for an insoluble active substance of the first or second embodiment in which the phospholipid comprises one or more selected from the group consisting of hydrogenated lecithin, hydrogenated phosphatidylcholine, phosphatidylinositol, phosphatidylethanolamine, and phosphatidylglycerol.

The fourth embodiment provides the carrier for an insoluble active substance of any one of the first to third embodiments in which the single chain nonionic surfactant comprises one or more selected from the group consisting of PPG-based, PEG-based, polysorbate-based, polyglyceryl-based, saccharide-based and biological surfactants.

A fifth embodiment provides the carrier for an insoluble active substance of any one of the first to fourth embodiments in which the single chain nonionic surfactant comprises one or more selected from the group consisting of PPG-13-decyltetradeceth-24, PEG-60 hydrogenated castor oil, PEG-40 hydrogenated castor oil, polysorbate 20, PPG polyglyceryl-6 caprylate, polyglyceryl-stearate, polyglyceryl-10 laurate, isotrideceth-9, sucrose stearate, sodium surfactin, nonadecanoyl nitrilo triacetic acid, arachidonoyl nitrilo triacetic acid, pentacosanoyl nitrilo triacetic acid and pentacosadiynoyl nitrilo triacetic acid.

A sixth embodiment provides the carrier for an insoluble active substance of any one of the first to fifth embodiments in which the phospholipid and the single chain nonionic surfactant are regularly or irregularly intersected in the bilayer structure.

A seventh embodiment provides the carrier for an insoluble active substance of any one of the first to sixth embodiments in which a weight ratio of the phospholipid and the single chain nonionic surfactant is 1:1 or more.

An eighth embodiment provides the carrier for an insoluble active substance of any one of the first to seventh embodiments in which a weight ratio of the phospholipid and the single chain nonionic surfactant is 1:1 to 20.

A ninth embodiment provides the carrier for an insoluble active substance of any one of the first to eighth embodiments in which the insoluble active substance is entrapped in the bilayer structure.

A tenth embodiment provides the carrier for an insoluble active substance of any one of the first to ninth embodiments in which the carrier further comprises an oil in the bilayer structure.

An eleventh embodiment provides the carrier for an insoluble active substance of any one of the first to tenth embodiments in which the oil comprises one or more of a hydrocarbon-based oil and a silicone-based oil.

A twelfth embodiment provides the carrier for an insoluble active substance of any one of the first to eleventh embodiments in which the oil comprises one or more selected from the group consisting of squalane, caprylic/capric triglyceride, cetyl ethylhexanoate, dibutyl adipate, neopentyl glycol diheptanoate, butylenes glycol dicaprylate/dicaprate, phenyl trimethicone, methyl trimethicone, cyclopentasiloxane, cyclohexasiloxane, caprylyl methicone, dimethicone and trisiloxane.

According to any one of the first to twelfth embodiments, a thirteenth embodiment provides the carrier for an insoluble active substance comprising the transfersome comprising the bilayer structure having the phospholipid and two or more single chain nonionic surfactants, wherein the hydrophobic tail of one or more single chain nonionic surfactants among the two or more single chain nonionic surfactants has a different number of carbon atoms than the hydrophobic tail of the phospholipid.

A fourteenth embodiment provides the carrier for an insoluble active substance of any one of the first to thirteenth embodiments in which the two or more single chain nonionic surfactants have different hydrophile-lipophile-balance (HLB) value from each other.

A fifteenth embodiment provides the carrier for an insoluble active substance of any one of the first to fourteenth embodiments in which a difference in HLB values between the two or more single chain nonionic surfactants is 1.5 or more.

A sixteenth embodiment provides the carrier for an insoluble active substance of any one of the first to fifteenth embodiments in which a particle size of the carrier for an insoluble active substance is 5 to 20 nm.

A seventeenth embodiment provides the carrier for an insoluble active substance of any one of the first to sixteenth embodiments in which the insoluble active substance is an oil-soluble, hydrophobic or water-insoluble active substance.

An eighteenth embodiment the carrier for an insoluble active substance of any one of the first to seventeenth embodiments in which the insoluble active substance comprises one or more selected from the group consisting of phytosterol, phytosphingosine, salicyloyl phytosphingosine, thymol trimethoxycinnamate, ceramide NP, ceramide NS, ceramide AS, ceramide AP, ceramide EOP, hydroxypropyl bislauramide MEA, hydroxypropyl bispalmitamide MEA, asiaticoside, asiatic acid, madecassic acid and ferulic acid.

According to any one of the first to eighteenth embodiments, a nineteenth embodiment provides a composition comprising the carrier for an insoluble active substance and an insoluble active substance.

The twentieth embodiment provides the composition of the nineteenth embodiment in which the composition comprises 0.001% by weight to 10% by weight of the insoluble active substance based on a total weight of the composition.

The twenty first embodiment provides the composition of the nineteenth or twentieth embodiment in which a total weight ratio of the carrier for an insoluble active substance to a total weight of the insoluble active substance comprised in the composition is 1:1 to 100.

The twenty second embodiment provides the composition of any one of the nineteenth to twenty first embodiments in which the oil comprised in the carrier for an insoluble active substance is comprised in an amount of 0.001% by weight to 10% by weight based on a total weight of the composition.

A twenty third embodiment provides the composition of any one of the nineteenth to twenty second embodiments in which the composition is an external preparation for skin.

A twenty fourth embodiment provides the composition of any one of the nineteenth to twenty third embodiments in which the composition is a cosmetic composition.

A twenty fifth embodiment provides the composition of any one of the nineteenth to twenty fourth embodiments in which the composition is a pharmaceutical composition.

What is claimed is:

1. A carrier for an insoluble active substance, comprising:
a transfersome comprising a bilayer structure having a phospholipid and a single chain nonionic surfactant,
wherein the phospholipid is a saturated phospholipid, and
wherein a difference in carbon numbers between a hydrophobic tail of the phospholipid and a hydrophobic tail of the single chain nonionic surfactant is 3 or more, and
wherein the hydrophobic tail of the phospholipid is longer than the hydrophobic tail of the single chain nonionic surfactant.

2. The carrier for an insoluble active substance according to claim 1, wherein the phospholipid comprises one or more selected from the group consisting of hydrogenated lecithin, hydrogenated phosphatidylcholine, phosphatidylinositol, phosphatidylethanolamine, and phosphatidylglycerol.

3. The carrier for an insoluble active substance according to claim 1, wherein the single chain nonionic surfactant comprises one or more selected from the group consisting of PPG-based, PEG-based, polysorbate-based, polyglyceryl-based, saccharide-based, and biological surfactants.

4. The carrier for an insoluble active substance according to claim 1, wherein the single chain nonionic surfactant comprises one or more selected from the group consisting of PPG-13-decyltetradeceth-24, PEG-60 hydrogenated castor oil, PEG-40 hydrogenated castor oil, polysorbate 20, PPG polyglyceryl-6 caprylate, polyglyceryl-10 stearate, polyglyceryl-10 laurate, isotrideceth-9, sucrose stearate, sodium surfactin, nonadecanoyl nitrilo triacetic acid, arachidonoyl nitrilo triacetic acid, pentacosanoyl nitrilo triacetic acid, and pentacosadiynoyl nitrilo triacetic acid.

5. The carrier for an insoluble active substance according to claim 1, wherein the phospholipid and the single chain nonionic surfactant are regularly or irregularly intersected in the bilayer structure.

6. The carrier for an insoluble active substance according to claim 1, wherein a weight ratio of the phospholipid and the single chain nonionic surfactant is 1:1 or more.

7. The carrier for an insoluble active substance according to claim 1, wherein a weight ratio of the phospholipid and the single chain nonionic surfactant is 1:1 to 20.

8. The carrier for an insoluble active substance according to claim 1, wherein the insoluble active substance is entrapped in the bilayer structure.

9. The carrier for an insoluble active substance according to claim 1, further comprising an oil in the bilayer structure.

10. The carrier for an insoluble active substance according to claim 9, wherein the oil comprises one or more of a hydrocarbon-based oil and a silicone-based oil.

11. The carrier for an insoluble active substance according to claim 10, wherein the oil comprises one or more selected from the group consisting of squalane, caprylic/capric triglyceride, cetyl ethylhexanoate, dibutyl adipate, neopentyl glycol diheptanoate, butylenes glycol dicaprylate/dicaprate, phenyl trimethicone, methyl trimethicone, cyclopentasiloxane, cyclohexasiloxane, caprylyl methicone, dimethicone, and trisiloxane.

12. The carrier for an insoluble active substance according to claim 1, wherein the bilayer structure comprises two or more of the single chain nonionic surfactants,
wherein a difference in carbon numbers between the hydrophobic tail of one or more of the single chain nonionic surfactants among the two or more of the single chain nonionic surfactants and the hydrophobic tail of the phospholipid is 3 or more, and
wherein the hydrophobic tail of the phospholipid is longer than the hydrophobic tail of the one or more of the single chain nonionic surfactants among the two or more of the single chain nonionic surfactants.

13. The carrier for an insoluble active substance according to claim 12, wherein the two or more single chain nonionic surfactants have different hydrophile-lipophile-balance (HLB) values.

14. The carrier for an insoluble active substance according to claim 13, wherein a difference in the HLB values of the two or more single chain nonionic surfactants is 1.5 or more.

15. The carrier for an insoluble active substance according to claim 1, wherein a particle size of the carrier for an insoluble active substance is 5 to 20 nm.

16. The carrier for an insoluble active substance according to claim 1, wherein the insoluble active substance is an oil-soluble, hydrophobic or water-insoluble active substance.

17. The carrier for an insoluble active substance according to claim 1, wherein the insoluble active substance comprises one or more selected from the group consisting of phytosterol, phytosphingosine, salicyloyl phytosphingosine, thymol trimethoxycinnamate, ceramide NP, ceramide NS, ceramide AS, ceramide AP, ceramide EOP, hydroxypropyl bislauramide MEA, hydroxypropyl bispalmitamide MEA, asiaticoside, asiatic acid, madecassic acid, and ferulic acid.

18. A composition comprising the carrier for an insoluble active substance of claim 1 and the insoluble active substance.

19. The composition according to claim 18, wherein a total weight ratio of the carrier for an insoluble active substance to a total weight of the insoluble active substance comprised in the composition is 1:1 to 100.

\* \* \* \* \*